Aug. 22, 1967 R. H. GAST Plant Pat. 2,761
HIBISCUS PLANT
Filed May 23, 1966
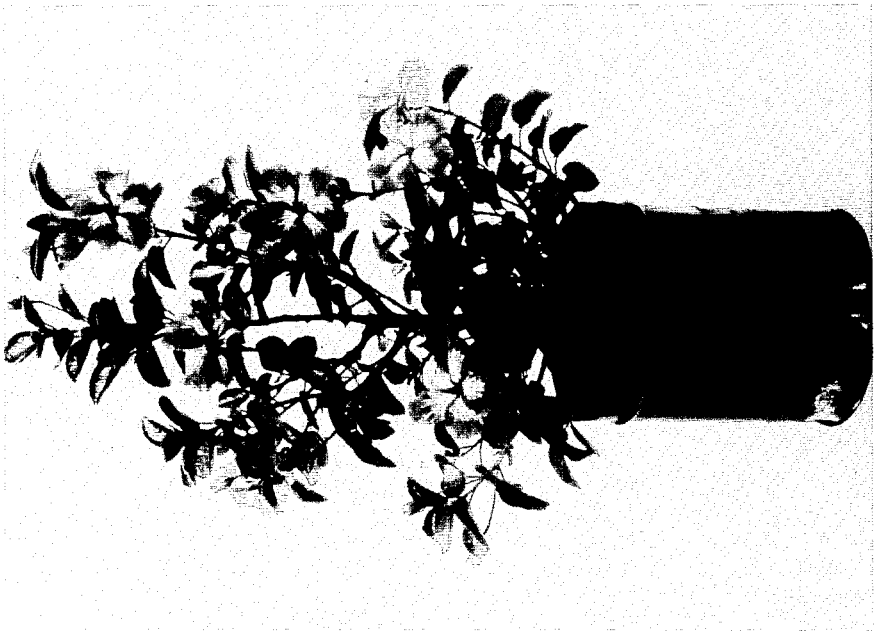
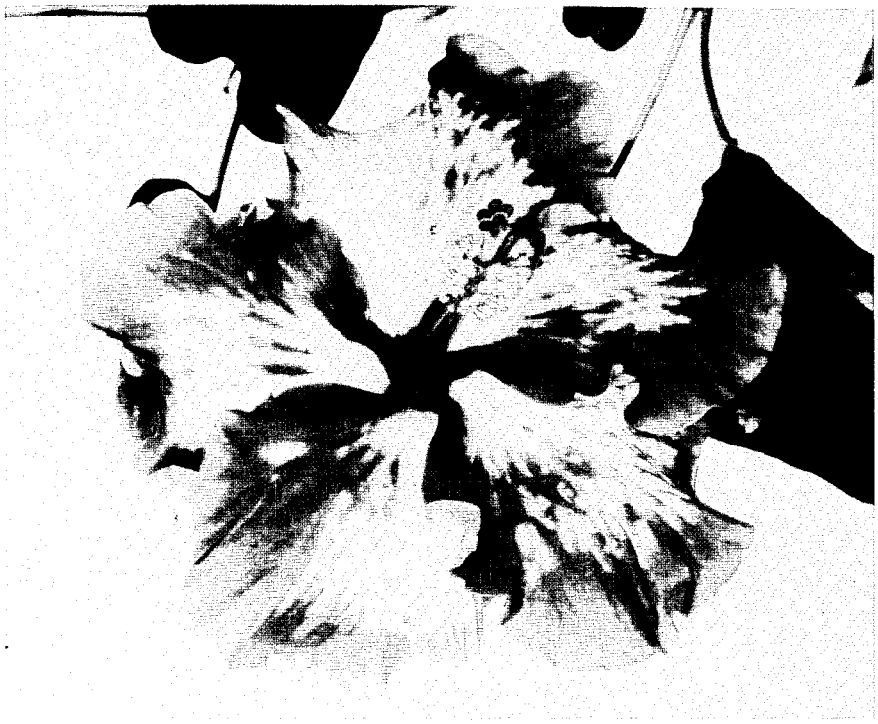
INVENTOR.
ROSS H. GAST,
By Edmond F. Shanahan.
ATTORNEY.

United States Patent Office

Plant Pat. 2,761
Patented Aug. 22, 1967

2,761
HIBISCUS PLANT

Ross H. Gast, Los Angeles, Calif., assignor to Monrovia Nursery Co., Azusa, Calif., a corporation of California Filed May 23, 1966, Ser. No. 552,352
1 Claim. (Cl. Plt.—54)

The present invention relates to a new and distinct variety of hibiscus plant, of the *Rosa-sinensis* species.

The plant is characterized as to novelty by its upright compact habit of growth, a special pattern of vivid coloring of the flowers, and foliage of an unusually bright green.

This plant appeared as a seedling in 1956, after extensive breeding efforts. It was observed to have distinct differences from the closest known hibiscus, Hibiscus Jack Frost. The plant will not come true from seed; it can be truly reproduced only by asexual means, that is by grafting and cutting.

A plant and flower of the new variety are shown in full color in the accompanying illustration.

A detailed description of the new variety follows, and to facilitate identification of the important colors, the color terminology adopted by the British Horticultural Color Charts has been followed. (Reference is to "Horticultural Color Charts" issued by the British Color Council in two volumes, in collaboration with the Royal Horticultural Society, copyright by Robert F. Wilson, published 1938–41.)

*The plant*

Parentage: Seedling resulting from definite breeding efforts.

*Pollen parent.*—Jack Frost.

*Seed parent.*—Barbara Buff.

Growth: The plant is of moderately vigorous, upright growth, well-clothed with foliage. The ultimate height of the plant is not known, but under normal conditions it should reach a height of 5 to 6 feet, with a spread of 3 to 4 feet.

Branches: New branch growth is a light green, Scheeles Green 860, changing to a light brown color as it matures. Bark is slightly rough.

Growth habit: Branching begins just above the ground level and has a tendency to ascend.

Foliage: The leaves are of good substance and are glossy.

*Shape.*—The leaves are best described as being broadly ovate, with the edges being somewhat involute. Margins are entire or occasionally toothed. The apex of the leaf is broadly acuminate; the base is truncate.

*Color.*—The upper surface of the leaf is Spinach Green o960/1; while the underside is Scheeles Green 860/1.

*Size.*—Leaves are from 3¼ to 4 inches in length and from 2 to 2¾ inches in width. The petiole is ¾ inch in length.

*Arrangement.*—Leaves are alternate on stems.

*Veins.*—The underside of each leaf has prominent veins which extend from the base of the leaf. The veins are slightly darker in color than the underside of the leaf.

*The flower*

The plant blooms in great abundance from May through October in southern California, with lighter bloom until the advent of colder weather.

Form: Flowers open wide and are from 4 to 5 inches in width.

Petals: Petals are five in number and are overlapping, with the tips slightly reflexed.

Color: The base of the petals is Current Red 821. This color graduates to Crimson 22/1 towards the edge of the petal. This color combination covers about two-thirds of the surface of each petal. One-third of the surface of the petal is covered by a blotch of white, which extends nearly to the uppermost edge of the petal. The backs of the petals are half Fawn Brown and half Crimson 22/2.

Stigma pads: Stigma pads are Orient Red 819/3.

Style: Style is Current Red 821 at the base, shading to Crimson 22/1 at the tip. Length of style is 2½ inches.

I claim:

A new and distinct variety of hibiscus plant, of *Rosa-sinensis* species, substantially as herein described and illustrated, and characterized particularly as to novelty by its upright, compact habit of growth, a special pattern of vivid coloring of the flowers, and foliage of an unusually bright green.

No references cited.

ABRAHAM G. STONE, *Primary Examiner.*

ROBERT E. BAGWILL, *Examiner.*